United States Patent [19]

Hauck et al.

[11] Patent Number: 4,501,011

[45] Date of Patent: Feb. 19, 1985

[54] ANGULATING LATERAL FLUOROSCOPIC SUSPENSION

[75] Inventors: Robert B. Hauck, Delafield; Larry Susami, Wauwatosa, both of Wis.

[73] Assignee: General Electric Company, Schenectady, N.Y.

[21] Appl. No.: 421,603

[22] Filed: Sep. 22, 1982

[51] Int. Cl.³ .............................................. G03B 41/16
[52] U.S. Cl. .................................. 378/196; 378/190; 378/197
[58] Field of Search ................ 378/196, 197, 189, 190

[56] References Cited

U.S. PATENT DOCUMENTS 2,818,510  12/1957  Verse ................................... 378/197
4,024,401  5/1977  Bernstein ............................ 378/197

Primary Examiner—Craig E. Church
Attorney, Agent, or Firm—Fuller, House & Hohenfeldt

[57] ABSTRACT

Means for coupling an independently suspended medical x-ray source and detector for lateral fluorographic studies such as angiography. When coupled, the x-ray source and detector move vertically in opposite directions, move horizontally toward or away from each other, and pivot about horizontal axes so the distances between the focal spot and isocenter of examination and between the isocenter and image each remain constant, and so the central ray of the source coincides with the central ray of the detector. The bridge also rotates to rotate the entire assembly about a vertical axis passing through the isocenter.

The x-ray source and detector are independently hung from the ceiling to support them directly above their centers of weight, eliminating the bending moments and oscillation which are inherent features of prior C-arm structures.

23 Claims, 13 Drawing Figures

ANGULATING LATERAL FLUOROSCOPIC SUSPENSION

BACKGROUND OF THE INVENTION

This invention relates to medical diagnostic x-ray apparatus, particularly apparatus for performing angiography.

In angiography procedures it is frequently necessary to obtain simultaneous x-ray views of the blood vessels in two different directions, such as in the posteroanterior direction and in the lateral direction. Apparatus which permits postero-anterior views is shown in U.S. Ser. No. 202,094, filed by Stivender et al. on Oct. 31, 1980 now U.S. Pat. No. 4,358,856 and assigned to the owner of the present invention. That application is incorporated herein by reference in its entirety to explain the construction and operation of the L-U arm apparatus for taking such views.

Two approaches are currently used for taking simultaneous lateral views. In the first approach, an x-ray source hung from the ceiling is positioned on one side of the patient and a freestanding x-ray detection device is positioned on the other side of the patient. As is well known, the freestanding detector and its associated electrical cables prevent the physician from moving freely around the patient and can also interfere with the source or detector for taking postero-anterior views. Another deficiency of this apparatus is that the source and detector for lateral views must be aligned manually.

Figure 12:
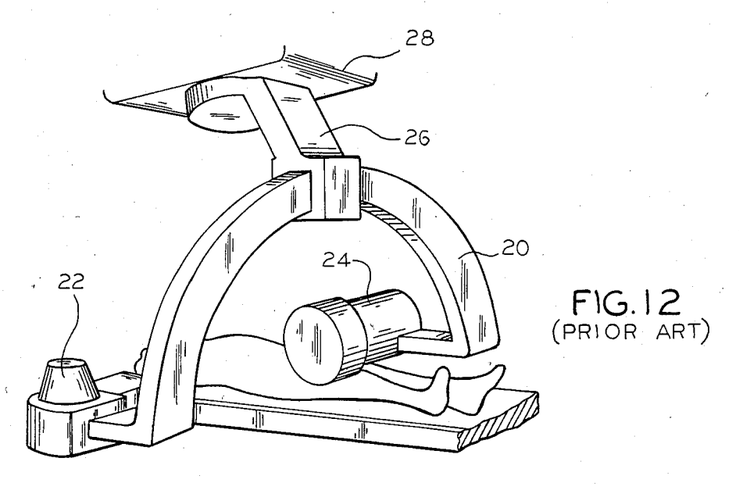
FIGS. 12 and 13 are schematic perspective views showing two prior art structures. These views have already been discussed in the preceding Background of the Invention section.
Figure 13:
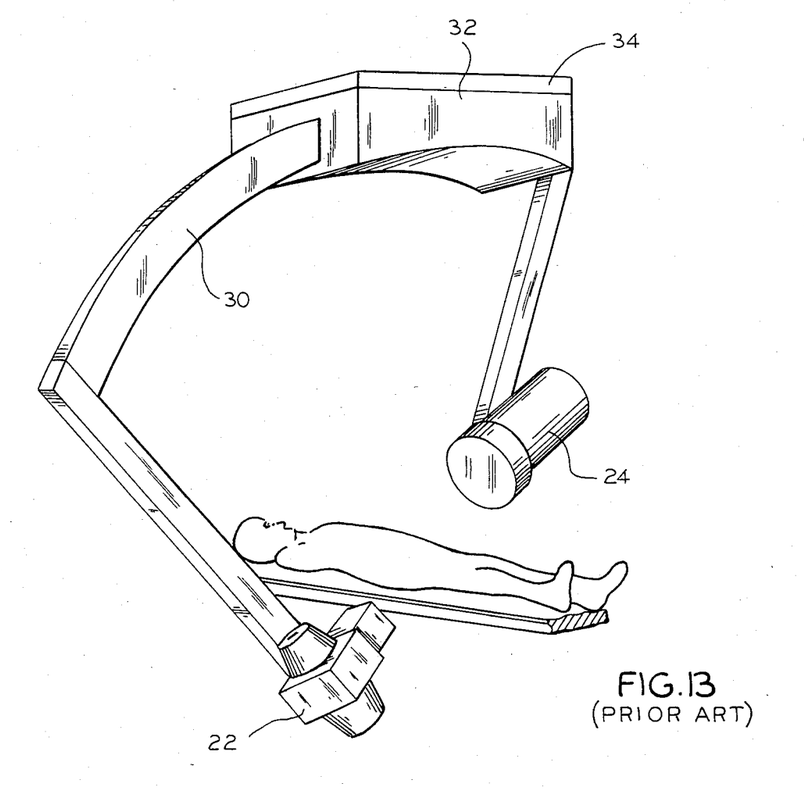

A second approach is shown in FIGS. 12 and 13, illustrating two prior art devices. In the device shown in FIG. 12, a single structural member 20 carries an x-ray source 22 and an electronic image intensifier 24 at its respective ends. Member 20 is supported by a brace 26 pivotally mounted to an overhead support 28 for rotating the pattern of radiation passing from source 22 to detector 24 about a vertical axis without disturbing the relative alignment of source and detector. In the embodiment shown in FIG. 13, source 22 and detector 24 are rigidly mounted to the respective ends of a rigid C-shaped member 30 received in a guide 32, which again is pivotally mounted to an overhead support 34. In this embodiment, member 30 can be rotated as before, or can be driven in either direction through guide 32 to rotate the pattern of x-rays passing between source 22 and detector 24 about the longitudinal axis of a patient.

The devices of FIGS. 12 and 13 seriously interfere with access to the patient by the physician, and when in motion can present a hazard to the patient and those working around the patient. Also, since in both prior art embodiments the mass of the x-ray tube and image intensifier is supported at a single point between them, support members 20 and 30 are prone to gravitational and inertial bending moments and oscillations which complicate the problem of aiming source 22 at detector 24. Furthermore, such devices can be disturbing to the patient, who is encircled by machinery. These structures also are difficult or impossible to move out of the way when they are not in use, as the entire assembly must be moved as a unit and cannot be retracted or collapsed to provide head room.

SUMMARY OF THE INVENTION

In accordance with the invention, an x-ray source is supported by a ceiling mounted carriage and telescoping hanger which permit the source to translate longitudinally, laterally, and vertically and to independently pivot about vertical and horizontal axes. An electronic image intensifier or other detector is supported in similar fashion by an independent carriage and telescoping hanger. When the x-ray source and image intensifier are to be used for conducting a lateral fluoroscopic examination, the respective carriages are coupled to a bridge member pivotally mounted to an overhead support.

The vertical positioning means for the respective hangers are linked when the source and detector are coupled to the bridge, so raising the source lowers the image intensifier, and vice versa. A mechanical linkage for moving the source and detector apart or together is coupled with the vertical positioning means so that, whether the central ray passing between the source and detector is disposed horizontally or not, the source and detector are always aimed at and diametrically opposed about an isocenter within the anatomy of interest. The pivoting of the source and detector about their horizontal longitudinal axes is correlated with the vertical positions of the source and detector on their hangers by electronic position sensing means which transmit signals indicating the relative elevation and pivotal positions of the source and detector.

As a result of the features described above, the source and detector are separable and can be retracted to the ceiling for compact storage when separated, and yet are mechanically linked when coupled to the bridge for tilting the central ray about vertical or longitudinal axes, permitting a wide selection of possible examination angles. The amount of equipment surrounding the patient is minimized, so access to the patient is maximized.

DESCRIPTION OF THE PREFERRED EMBODIMENT

Although the disclosure hereof is detailed and exact to enable those skilled in the art to practice the invention, the physical embodiments herein disclosed merely exemplify the invention, which may be embodied in other specific structure. While the best known embodiment has been described, the details may be changed without departing from the invention, which is defined by the claims.

Figure 1:
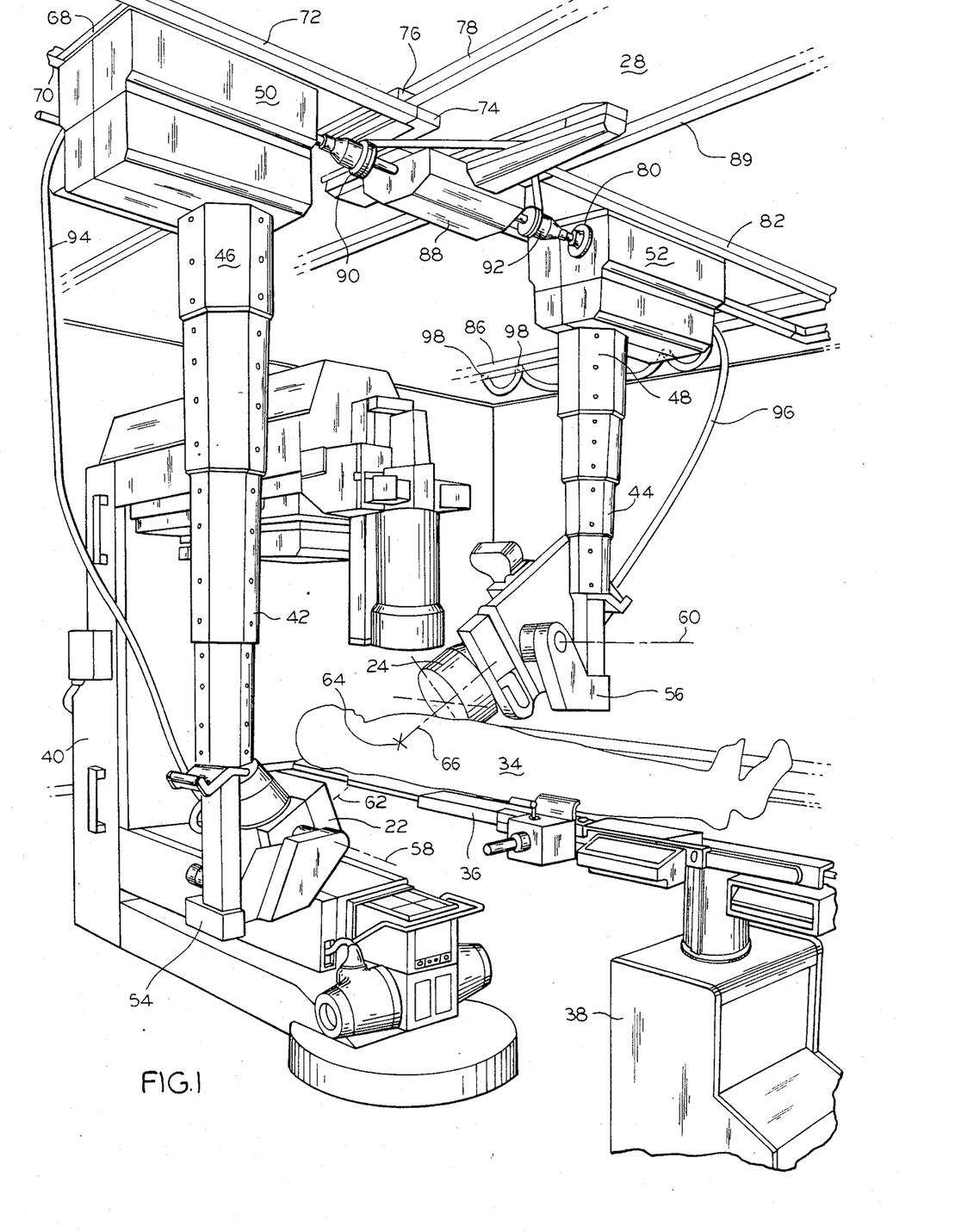
FIG. 1 is a perspective view of the present invention deployed in an examination room. A patient is shown positioned on an examination table and a known L-U arm assembly (40) is shown.

Referring first to FIG. 1, patient 34 is supported on an examination table 36 which is cantilevered with respect to its base 38 to permit the equipment to be positioned at various points with respect to the patient. An L-U arm x-ray apparatus 40 is supported by the floor of the room, and in this arrangement can be used for postero-anterior examination of the patient. A further description of apparatus 40 can be found in the patent application previously incorporated by reference. The illustrated examination room includes an overhead support 28, which in the illustrated embodiment is its ceiling.

An x-ray source 22 and an x-ray detector 24 (here, a low powered x-ray tube and an electronic image intensifier for fluorographic studies) are respectively supported by telescoping hangers 42, 44 having their respective upper ends 46, 48 secured to an x-ray source carriage 50 and x-ray detector carriage 52. The lower ends 54 and 56 of hangers 42 and 44 pivotally receive x-ray source 22 and image intensifier 24 so the latter elements can respectively rotate about an axis 58 (which is parallel to the longitudinal axis through patient 34 and passes through the focal spot of x-ray source 22) and an axis 60 which is parallel to axis 58.

Central ray 62 of the pattern of x-rays emitted from source 22 is aimed through an isocenter 64, as is the longitudinal axis 66 of image intensifier 24 (about which the x-ray pattern received and acted upon by image intensifier 24 is disposed). Source 22 and image intensifier 24 are supported adjacent to the respective lateral sides of patient 34.

Carriage 50 is pivotally mounted to a roller truck 68 which is captured by parallel arms 70 and 72 of a lateral track member 74 to permit lateral travel of carriage 50 and rotation of the carriage about a vertical axis. Lateral track member 74 is suspended from a pair of roller trucks such as 76 which travel on parallel, longitudinally disposed tracks such as 78 mounted to overhead support 28 for permitting track member 74, and thus roller track 68 and carriage 50, to travel longitudinally. This system provides direct support for x-ray source 22, and since hanger 42 is substantially vertical it has substantially no bending moment due to gravity.

Carriage 52 similarly is pivotally suspended from roller truck 80, lateral track member 82, and roller trucks secured to member 82 for traveling on tracks 84 and 86 mounted to overhead support 28.

Although independently supported, carriages 50 and 52 can be coupled to a bridge member 88 pivotally secured to overhead support 28 for rotation about a vertical axis passing through isocenter 64. The coupling sites are first and second coupling means generally indicated by reference characters 90 and 92. As will be seen, each coupling means includes male and female members which are coupled as shown in FIG. 1 to locate the carriages and uncoupled when the carriages are to be separated. When the couplings are separated the x-ray source and detector can be independently moved, and can even be pushed into different corners of the examination room for storage. The x-ray source can also be used independently of the image intensifier when uncoupled. For example, L-U arm 40 can be pivoted 90 degrees about its floor pivot, so x-ray source 22 can be aimed at a auxiliary detector mounted to arm 40 (as disclosed in the previously incorporated patent application).

Electric power and control cable bundles 94 and 96, containing conductors for providing electric power to x-ray source 22 and detector 24 and for operating the invention, are routed from source 22 and detector 24 to the respective carriages 50 and 52, and from there in helical coils supported by slides 98 carried in tracks such as 86 to a remote connection point (not shown).

Figure 2:
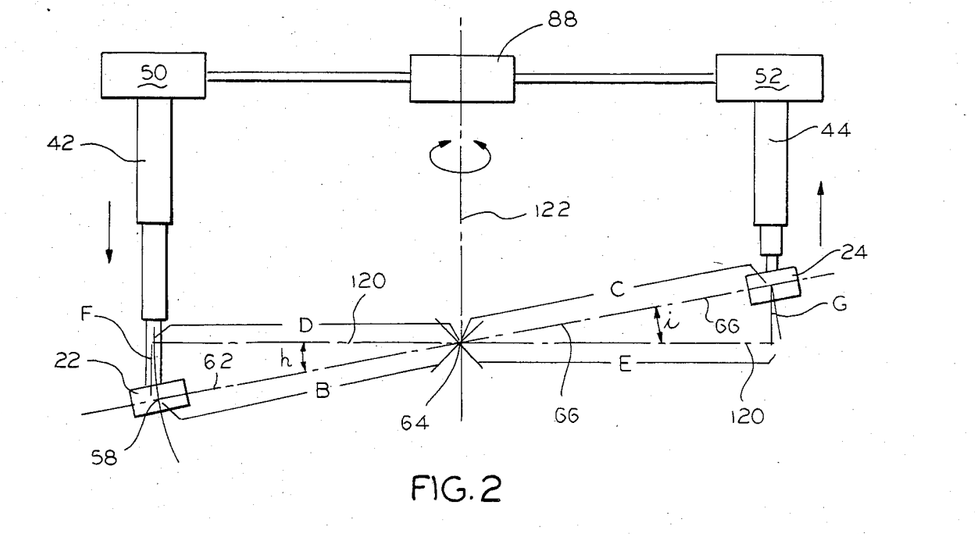
FIGS. 2 and 3 are diagrammatic rear elevational views of two positions of the structure shown in FIG. 1, illustrating the geometrical relations of the x-ray tube, detector, patient, and examination room according to the present invention.
Figure 3:
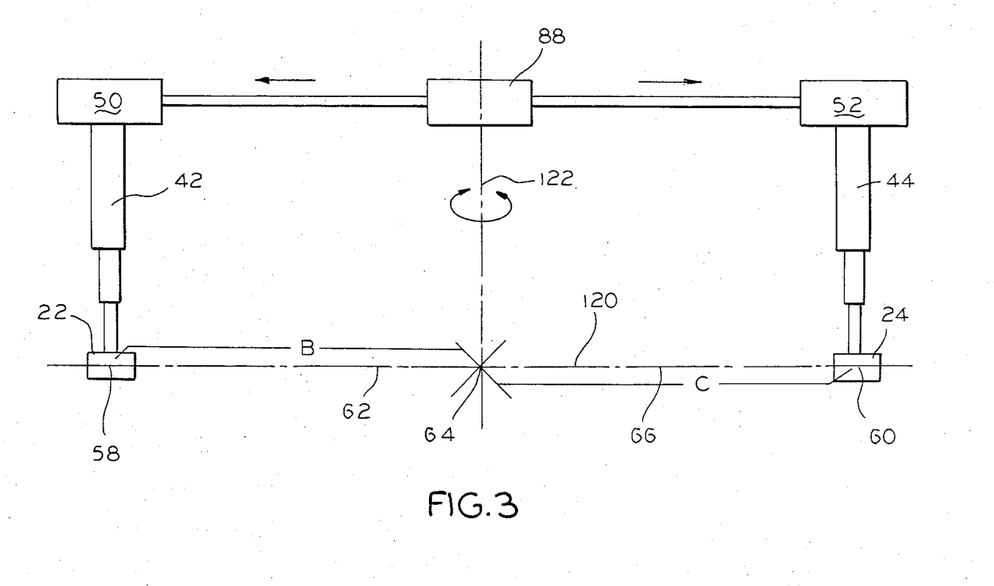

FIGS. 2 and 3 show several geometric relationships which are maintained by the illustrated embodiment. B is the distance from pivot axis 58 of x-ray source 22 to isocenter 64; C is the distance from pivot axis 60 to isocenter 64; D is the horizontal component of B and lies along a lateral axis 120 through isocenter 64; E is the horizontal component of C and also lies on axis 120; F is the vertical component of B; G is the vertical component of C; h is the angle between B and D; and i is the angle between C and E. Isocenter 64 is always stationary. B and C are always equal, and do not change for any position of the apparatus. F and h are respectively equal to G and i, and they all vary between zero (as in FIG. 3) and a positive value (as in FIG. 2). Thus, source 22 and image intensifier 24 are always diametrically opposed through isocenter 64 when coupled by bridge 88, and the source to image distance remains constant for any value of h and i. Central ray 62 and longitudinal axis 66 are always directed through isocenter 64 and are collinear. Finally, the entire assembly is rotatable as a rigid unit about a vertical axis 122 through isocenter 64.

To maintain the equality of F and G, source 22 and detector 24 are mechanically linked by bridge 88, carriages 50 and 52, and hangers 42 and 44 so raising either source 22 or detector 24 lowers the other by an equal amount. To keep B and C constant during such vertical travel, carriages 50 and 52 are translated toward bridge 88 when F and G are increased and away from bridge 88 when F and G are decreased. At the same time, microprocessor controlled servomechanisms aim source 22 and detector 24 toward isocenter 64 by varying h and i. The details of these mechanisms are shown in FIGS. 4–11.

In the illustrated embodiment, image intensifier 24 can translate along its longitudinal axis 66 with respect to hanger 44 to vary the isocenter to image distance without disturbing the foregoing relationships. This additional capability allows the magnification of the image to be varied without changing the other relationships just described.

Referring now to FIGS. 4–7, bridge 88 comprises a cross shaped horizontally disposed housing 130 mounted to overhead support 28 (FIG. 1) for pivoting about vertical axis 122 (which passes through isocenter 64). Housing 130 supports coaxial splined shafts 132 and 134. The inboard end 136 of shaft 132 is carried by ball bearings 138 and 140 mounted to a truck 142 having rollers such as 144, 146, 148, and 150 which permit slight vertical translation of truck 142 within housing 130. The outboard end of shaft 132 is a probe 152 for being received in the bore 154 of a tubular member 156.

Figure 4:
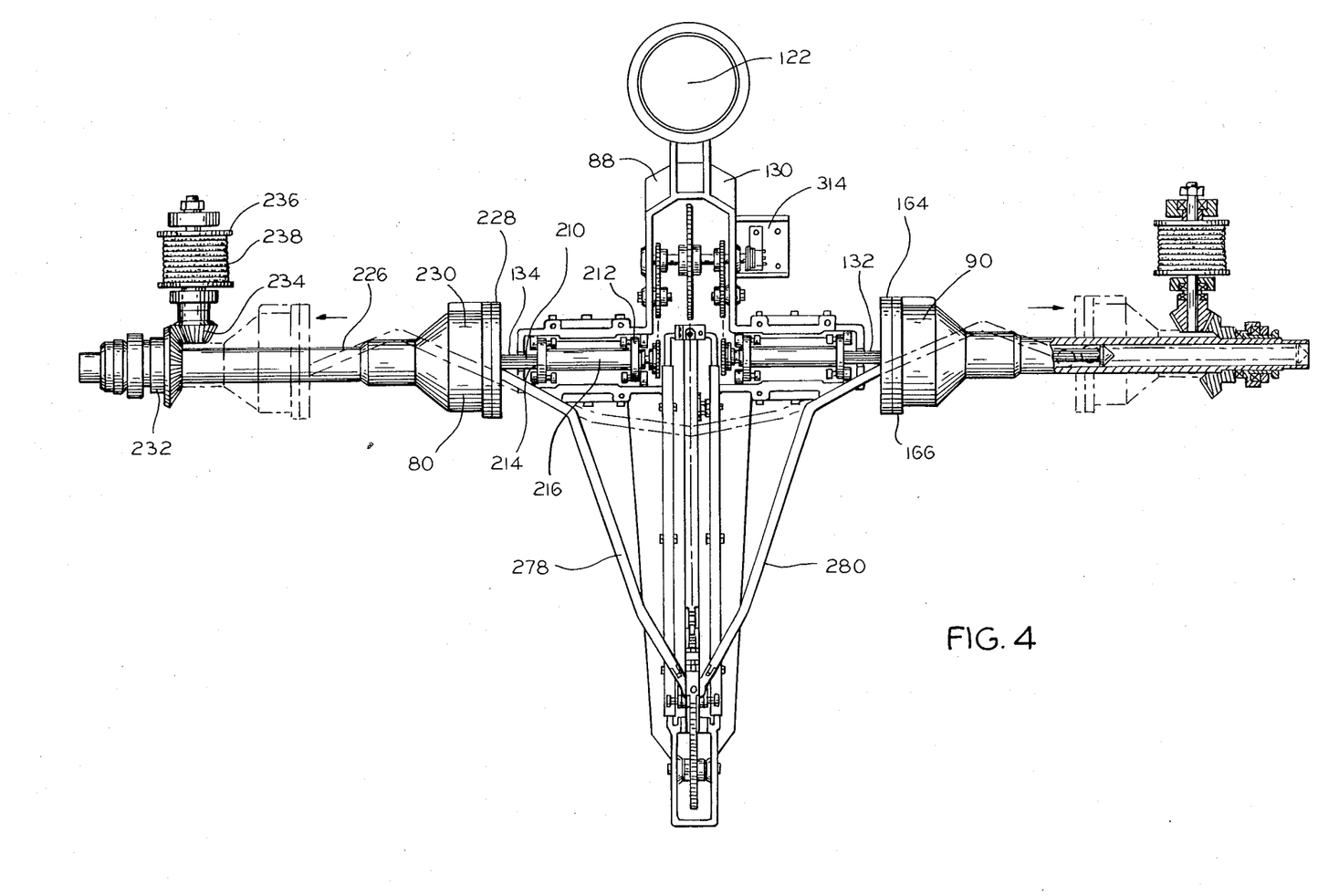
FIG. 4 is a fragmentary bottom plan view of the structure shown in FIG. 1, illustrating the mechanism for linking the x-ray source and detector together. Covers are removed and some parts are shown in section.
Figure 5:
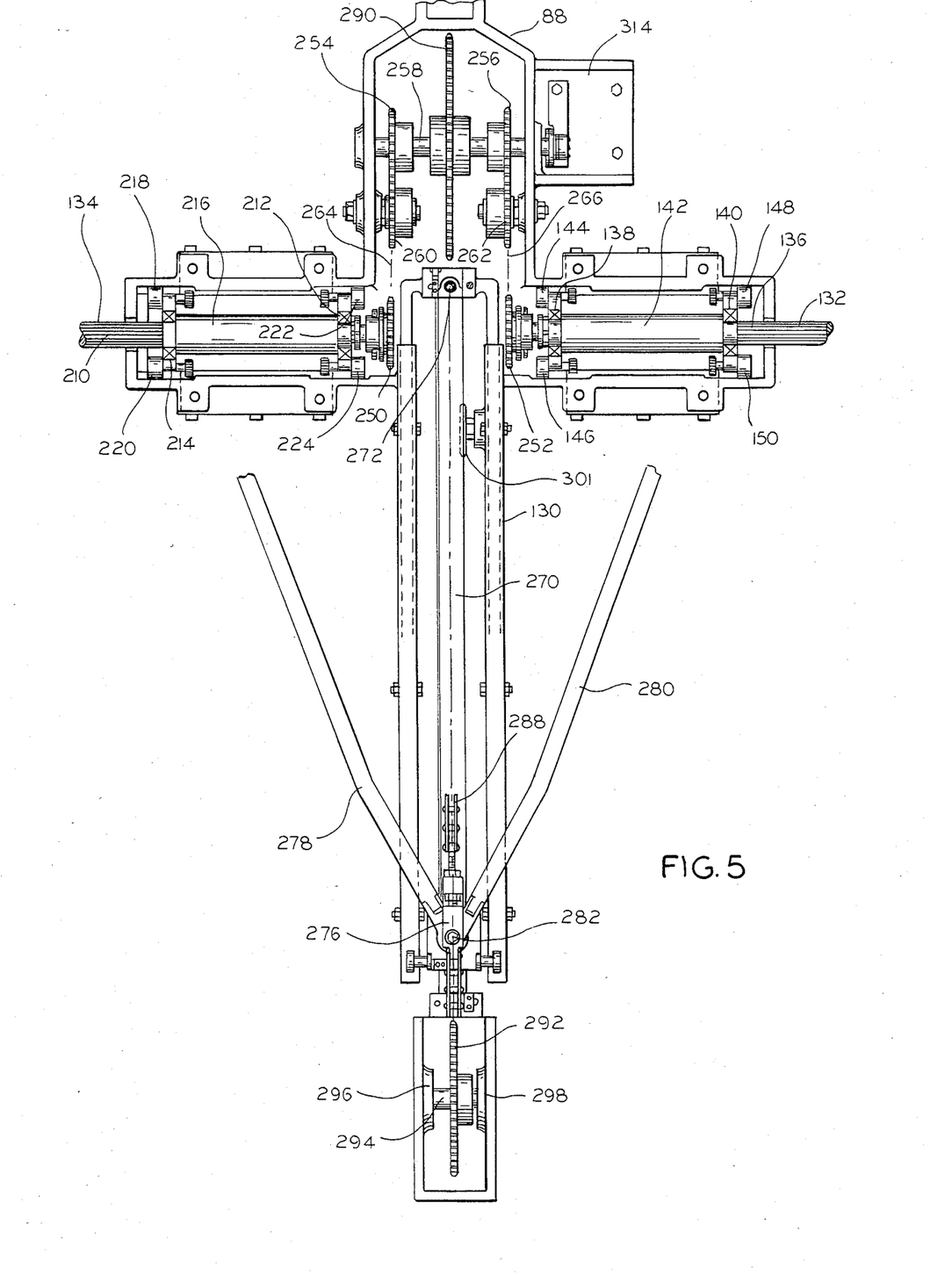
FIG. 5 is an enlarged detail view of the central portion of the structure shown in FIG. 4.
Figure 6:
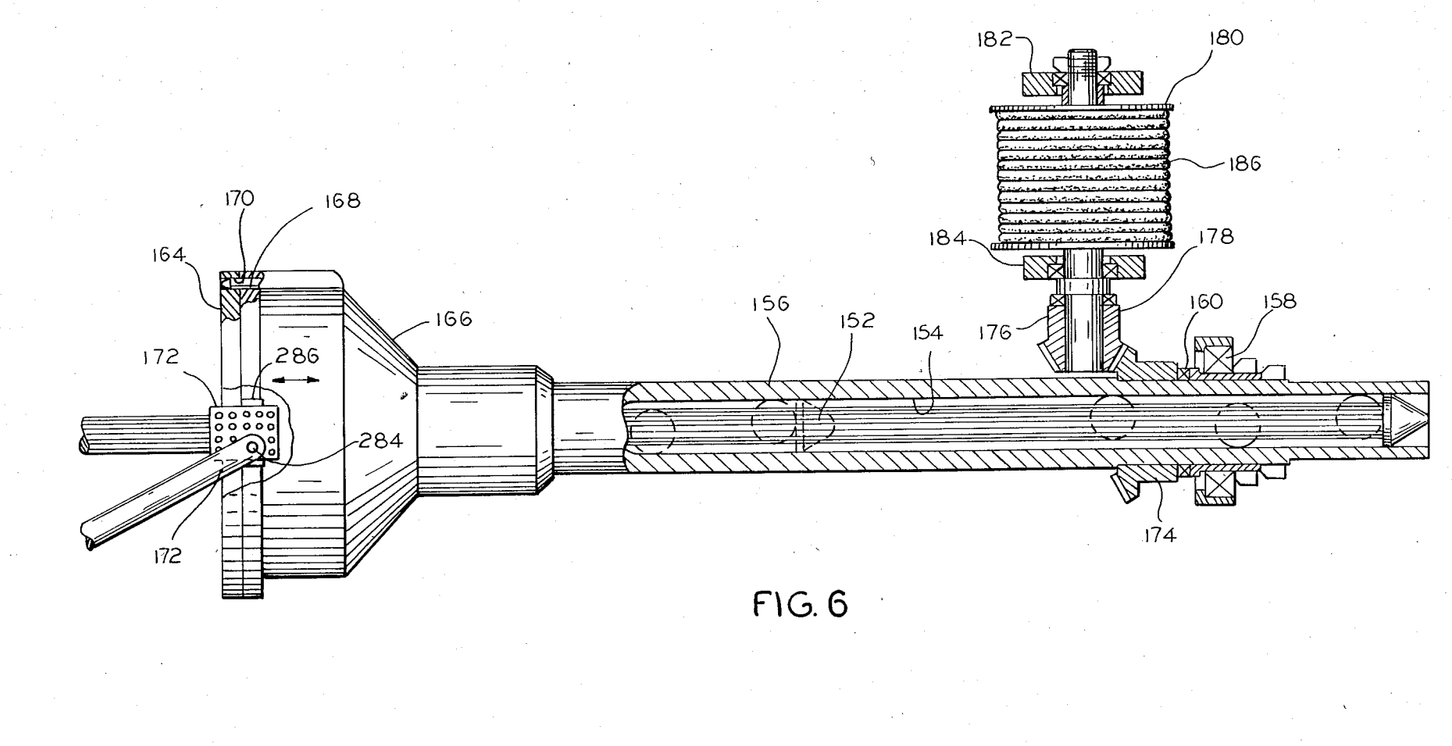
FIG. 6 is an enlarged detail view of an outside portion of the structure shown in FIG. 4.

Member 156 is supported partially within x-ray source carriage 50 by rotation and thrust bearings such as 158, 160. A first coupling member 164, here a male member, is splined to and slidable along shaft 132. Second coupling member 166 is a female member secured to member 156 to receive first coupling member 164. Second coupling member 166 includes a dog 168 for being received in a bore 170 in first coupling member 164 so when the coupling members are coupled they rotate together. Coupling members 164 and 166 are seated together when coupled by a ball detent mechanism. First coupling member 164 is linked to a slide 172 which is slidably carried on splined shaft 132. Tubular member 156 includes a coaxial bevel gear 174 that meshes with a bevel gear 176 secured to a shaft 178 to which a power take-off cable drum 180 is fixed. The cable drum shaft is rotatably secured to fixed members 182 and 184 of carriage 50 by thrust and rotation bearings.

Figure 8:
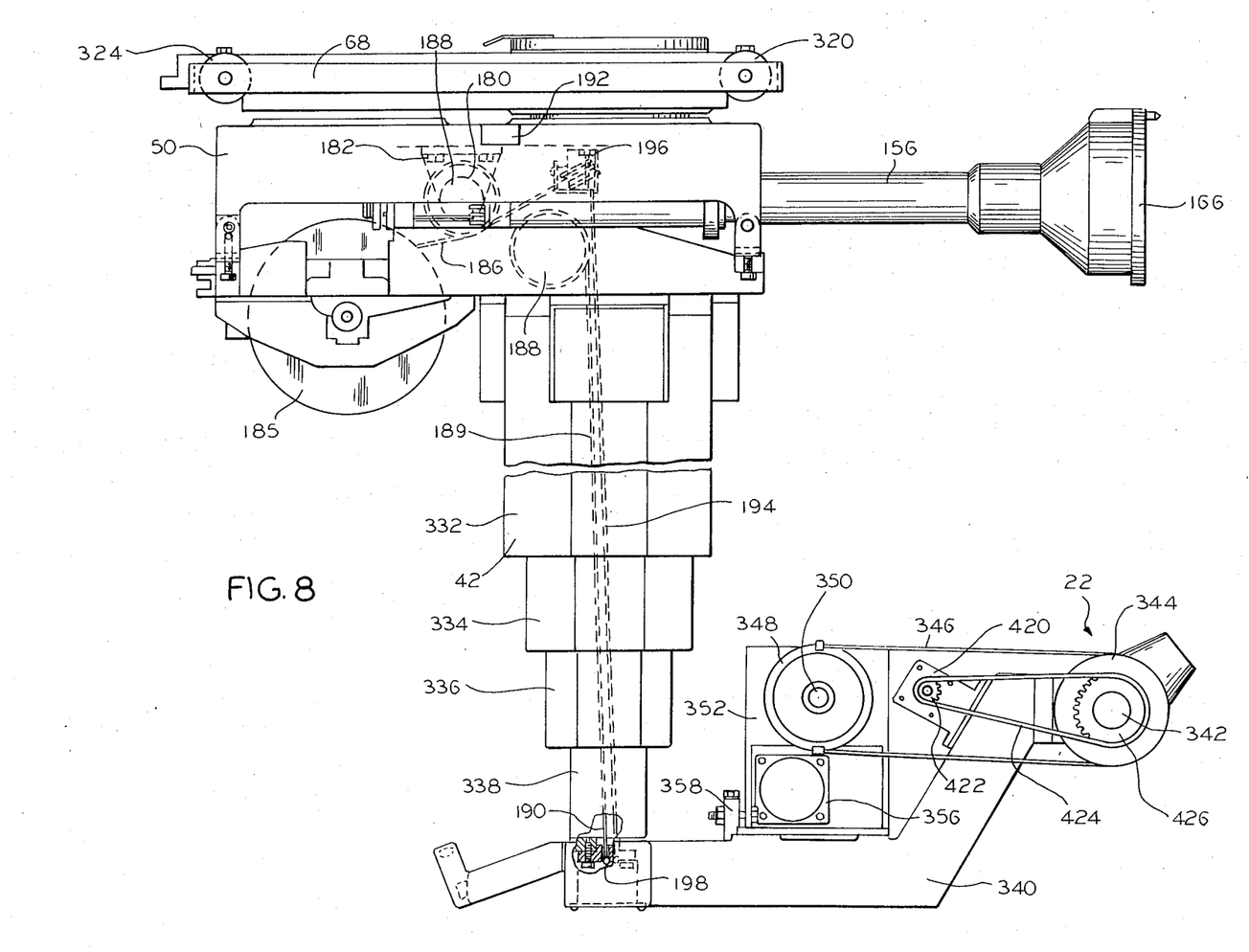
FIG. 8 is a rear elevational view of the x-ray tube hanger and carriage shown in FIG. 1, and is representative of the structure of the x-ray image intensifier hanger and carriage as well.

A counterpoise drum 185 is also mounted to carriage 50. A flat spiral torsion spring (not shown) has its respective ends secured to drum 185 and its supports for exerting a counterclockwise (as seen in FIG. 8) torque on drum 185. A cable 186 is wound on counterpoise drum 185, reeved about power take-off drum 180 and about an idler pulley 188, and has a vertical run 189 best seen in FIG. 8. The lower end 190 of run 189 is anchored to the lower arm of hanger 42. Winding cable 186 onto drum 185 by turning drum 180 with motor 303 of the coupling drive raises source 22 and collapses hanger 42, while rotating drum 180 in the other direction extends hanger 42 and thereby lowers source 22.

An encoder 192 is driven by an encoder cable 194 which is wound about another drum (not shown) fixed and coaxial with respect to power take-off drum 180. Cable 194 is run through direction changing block 196, and run vertically downward to an anchor 198 fixed to the lower arm of hanger 42. Encoder 192 is thus enabled to transmit a signal corresponding to the vertical position of source 22.

For each of the structures identified by reference numerals 136 through 198 there is a corresponding structure associated with splined shaft 134, carriage 52, and hanger 44, although some of the latter elements are not separately illustrated. Reference characters for the illustrated features are as follows: inboard end 210 of shaft 134; bearings 212 and 214; truck 216; rollers 218, 220, 222, and 224; tubular member 226; coupling members 228 and 230; bevel gears 232 and 234; cable drum 236 and cable 238.

Figures 7, 9:
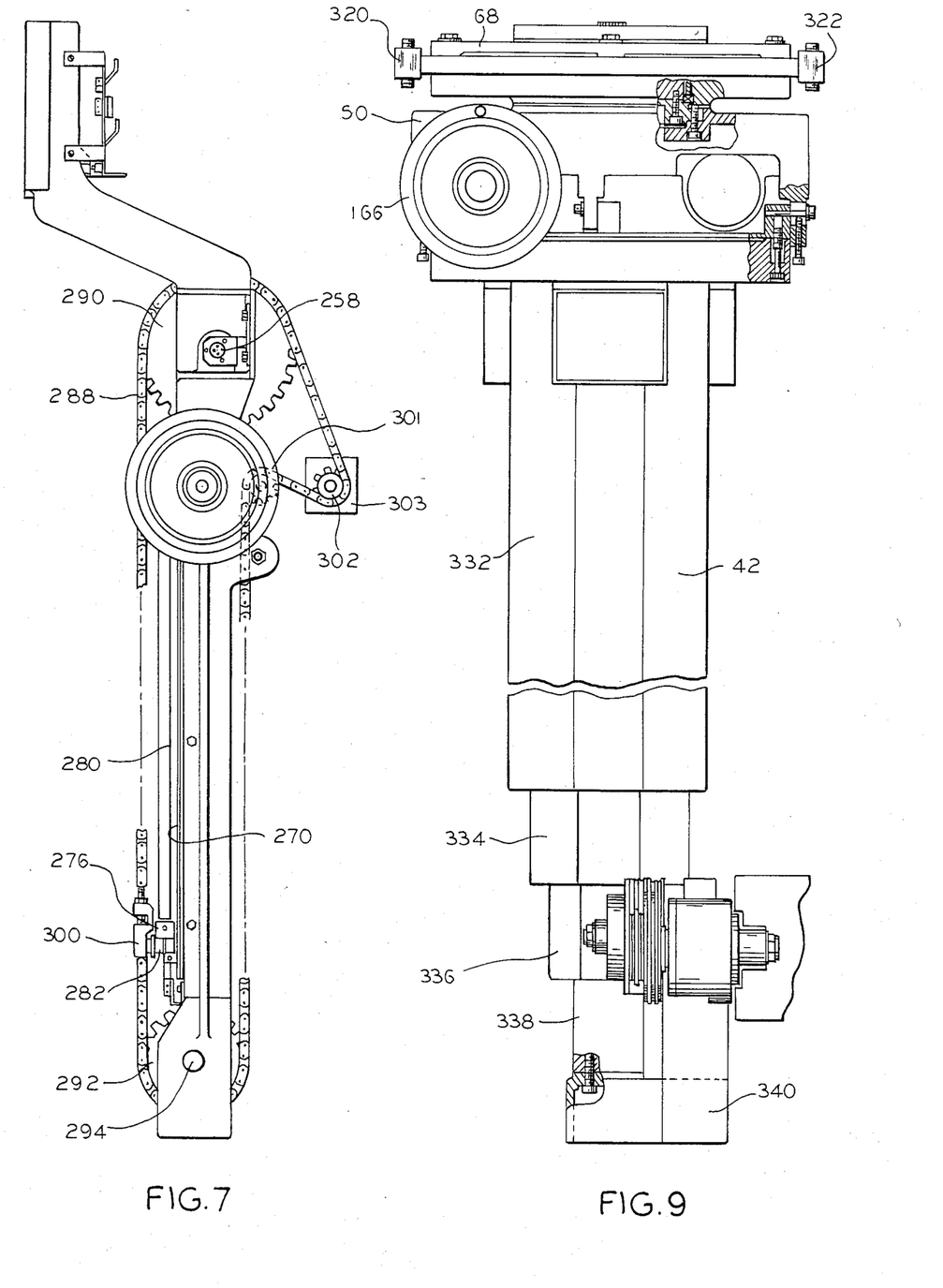
FIG. 7 is a fragmentary side elevational view of the structure shown in FIG. 4.
FIG. 9 is an inside elevational view of the structure shown in FIG. 8, with covers removed and the x-ray tube broken away.

A chain drive is provided to couple splined shafts 132 and 134 so they will rotate in the same direction at the same speed. Referring to FIGS. 4, 5, and 7, sprockets 250 and 252 are keyed to the inboard ends of splined shafts 132 and 134, sprockets 254 and 256 are keyed to a shaft 258 secured to bridge 88 for rotation, and chain tension adjusting sprockets 260 and 262 are rotatably and slidably carried on bridge 88. A first endless chain 264, trained about sprockets 250 and 254 and under sprocket 260, transmits the rotation of shaft 134 to shaft 258 (and vice versa), and an identical chain 266 transmits the rotation of shaft 132 to shaft 258 (and vice versa). When the carriages are coupled to the bridge, cable 186 is wound by drum 180 at the same rate that cable 220 is unwound by drum 218, and vice versa. The vertical travel of source 22 is thus equal and opposite to the vertical travel of image intensifier 24 when the assembly is coupled together as shown in the Figures.

The following mechanism is provided for spreading carriages 50 and 52 apart or drawing them together as required to keep the source to image distance constant despite relative vertical travel of the source and detector. A guide 270 is disposed perpendicularly to shafts 132 and 134 and is secured to bridge 88 by fasteners such as 272. A slide 276 is slidably carried on guide 270, and link arms 278 and 280 are each secured at one end by a pivot pin 282 to slide 276. The other ends of link arms 278 and 280 are secured by pivots 284 to the outer races of rotation bearings such as 286 carried on the respective slides such as 172. Slide 276 is driven by an endless drive chain 288 having its respective ends reeved about a sprocket 290 keyed to shaft 258 and a sprocket 292 rotatably carried by shaft 294 journaled in bearings 296 and 298 at the remote end of bridge 88. Referring to FIG. 7, a link 300 (which includes a chain tension adjustment) secures chain 288 to slide 276. Chain 288 is also reeved about an idler sprocket 301 rotatably secured to bridge 88 and about a drive sprocket 302 driven by a reversible servomotor 303. When sprocket 302 is driven one way by servomotor 303, slide 276 and link arms 278 and 280 move toward the position shown in phantom in FIG. 4, x-ray source 22 is raised, image intensifier 24 is lowered, and carriages 50 and 52 are spread apart as h and i decrease. Reversing the servomotor causes slide 276 and link arms 278 and 280 to approach the positions shown in full lines in FIG. 4, source 22 to be lowered, image intensifier 24 to be raised, and carriages 50 and 52 to be drawn together as h and i increase. When slide 276 is in the position shown in phantom in FIG. 4, that is, nearest shafts 132 and 134, link arms 278 and 280 and the carriages are spread to their maximum separation and source 22 and detector 24 are level with isocenter 64. The drive just described also includes a potentiometer 314 which senses and transmits the approximate rotational position of shaft 258, which in turn is directly related to the exact vertical positions of the x-ray source and detector (provided by their respective encoders such as 192) and the separation between coupled carriages 50 and 52.

Figure 10:
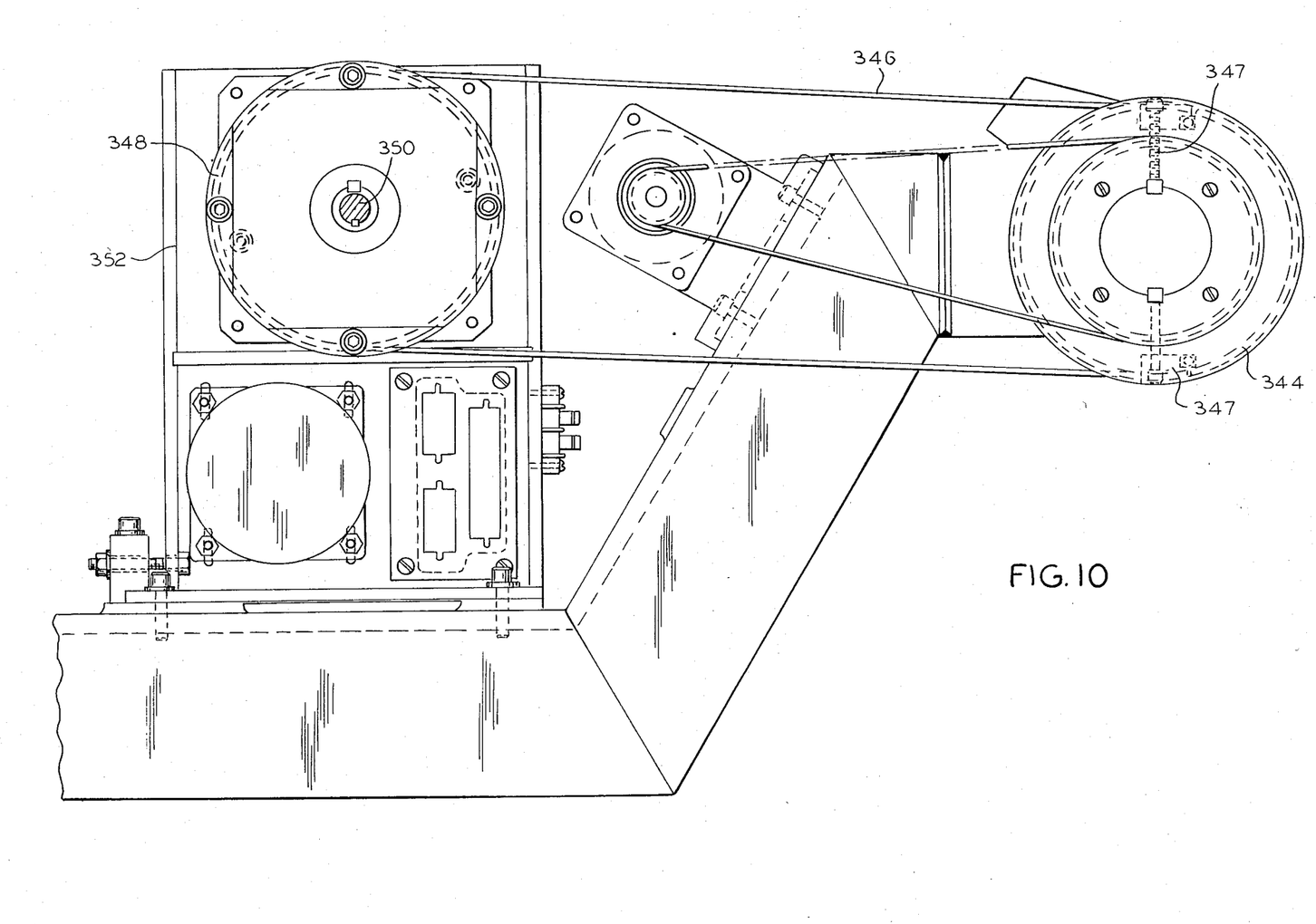
FIG. 10 is an enlarged detail view of the lower end of the x-ray tube hanger shown in FIG. 8.

FIGS. 8, 9, 10, and 11 illustrate details of hanger 42 and carriage 50. (Although hanger 44, carriage 52 and associated structures are not specifically shown, they are identical to the corresponding structures of hanger 42 and carriage 50 as described herein.) In addition to parts previously identified in the preceding disclosure, FIGS. 8 and 9 show that roller truck 68 includes roller assemblies such as 320, 322, and 324, of which rollers 320 and 324 are carried in track 72 and roller 322 is carried in track 70. Hanger 42 comprises telescoping segments 332, 334, 336, and 338, the latter secured to a horizontally and obliquely extending arm 340 supporting a pivot shaft 342 which is coaxial with the focal point of x-ray tube 22. A sheave 344 rotatably secured to shaft 342 receives a cable 346 having its respective ends 347 secured to sheave 344 as shown in FIG. 10. Cable 346 is driven by a sheave 348 mounted on a pivot shaft 350 rotatably carried by a frame 352 secured to arm 340. Sheave 348 is connected via a clutch and gear reduction 354 (shown in FIG. 11) to a reversible stepper motor 356 mounted to frame 352. Frame 352 can be made slidable with respect to arm 340 by loosening its fastenings for adjusting the tension of cable 346, and an adjustment mechanism 358 bearing between arm 340 and frame 352 is provided for that purpose.

Figure 11:
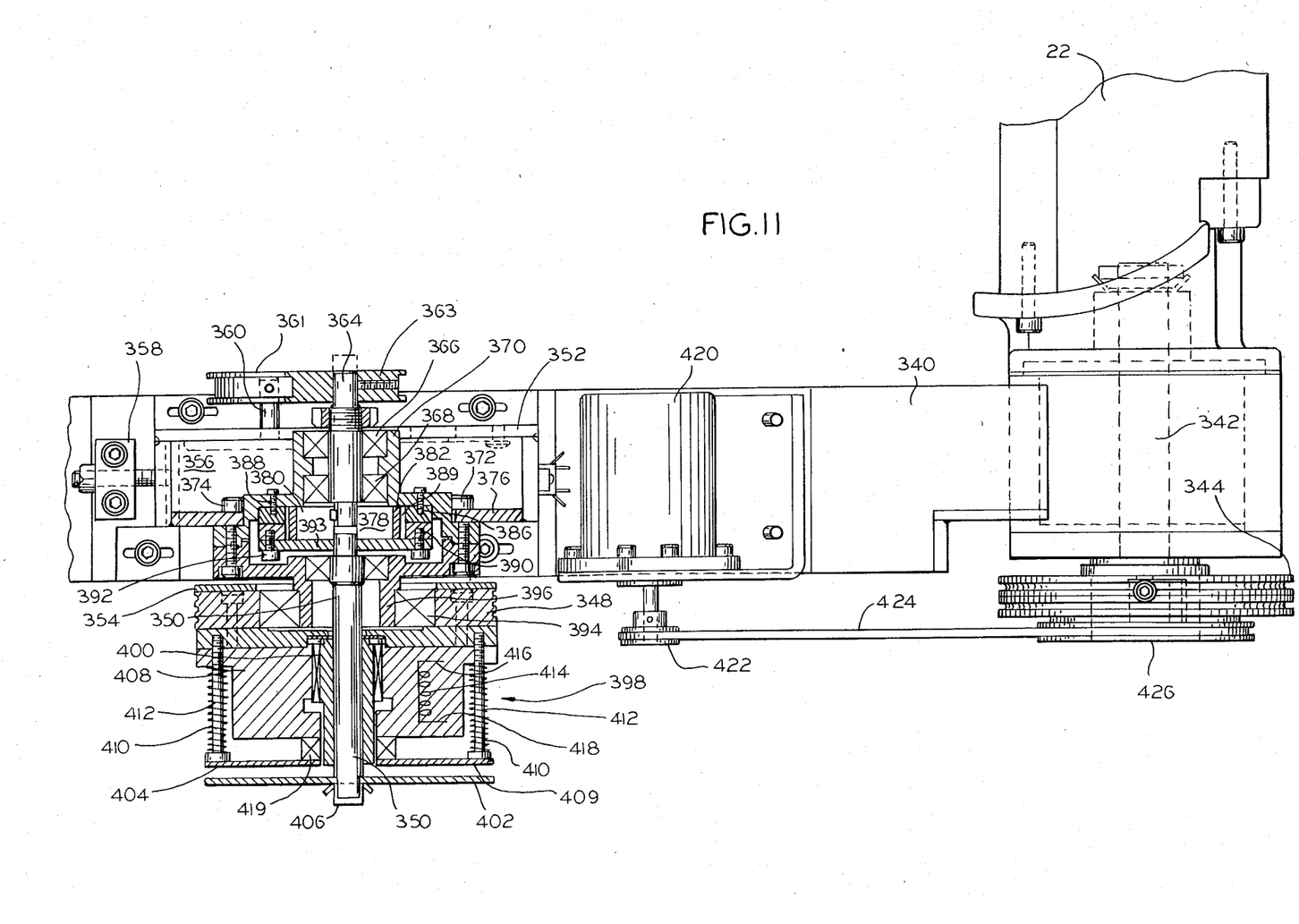
FIG. 11 is a top plan view, partly in section, of the structure shown in FIG. 10.

FIG. 11 shows the details of clutch and gear reduction 354. Cable 346 has been removed in FIG. 11 for greater clarity of illustration. Stepper motor 356 has an output shaft 360 secured to a sheave 361 which is connected via a drive belt (not shown, for clarity) to a sheave 363 secured to an input shaft 364 of a high ratio in line gear reduction set. Shaft 364 is carried by bearings 366, 368 secured to a fixed member 370. Member 370 is secured by fasteners 372, 374 to a member 376 of frame 352. Input shaft 364 is keyed to wave generator 378—a ball bearing having an elliptical inner race 380 and a flexible outer race 382. Race 382 is pressed into flexible spline ring 384, which has 240 teeth on its outside edge. Spline ring 384 is received within a fixed ring gear 386, having 242 internal teeth and secured by fasteners 388 to fixed member 370, and also within a rotating ring gear 390 having 240 internal teeth and secured by fasteners 392 to a disc 293 secured to pivot shaft 350. Rotation of elliptical race 380 flexes the teeth of diametrically opposed portions of spline ring 384 outwardly to sequentially mesh with the adjacent teeth of ring gears 386 and 390. Ring gear 386 is fixed and has two more teeth than spline 384, therefore permitting spline 384 to make two revolutions contrary to the rotation of inner race 380 for each 240 revolutions of inner race 380. Ring gear 390, which has the same number of teeth as spline 384, rotates at the same rate as spline 384. The resulting drive ratio is thus 240:2, or 120:1.

Pivot shaft 350 is supported by bearing 394 (secured to stationary member 396) and drives sheave 348 via a normally engaged clutch generally indicated at 398 (shown disengaged). Clutch 398 comprises a ferromagnetic plunger 400 splined to and axially slidable to a slight degree along pivot shaft 350; first and second clutch plates 402 and 404, the former secured to pivot shaft 350 by a retainer 406, the latter secured nonrotatably but axially movable relative to magnetic coil housing 408 (which in turn is secured to sheave 348); compression coil springs 412 carried on slidable guide shafts 410 and bearing between coil housing 408 and second clutch plate 404; and a conductive coil shown schematically at 414, having terminals 416 and 418 for being connected to a source of D.C. power. Bearing 419 transmits axial thrust but no torque between plunger 400 and clutch plate 404.

Clutch 398 is engaged when no power is fed to coil 414 because springs 412 urge clutch plate 402 against clutch plate 404. Because of the high gear reduction between shaft 360 and sheave 348, if stepper motor 356 is not energized and clutch 398 is engaged x-ray source 22 will maintain its pivotal position. By energizing coil 414, which counteracts the bias of springs 412 and thereby disengages the clutch plates, sheave 348, and thus sheave 344, are free to rotate to allow manual pivoting of the x-ray source.

The pivotal position of x-ray tube 22 is transmitted by a position encoder 420 via a timing pulley 422, timing belt 424, and a timing pulley 426 mounted on pivot shaft 342.

The x-ray image intensifier 24 includes essentially identical structure, including position encoders for hanger length and pivotal position, a gear reduction, a clutch, and frame elements, to allow it to be manually positioned when the clutch is disengaged and automatically positioned when the clutch is engaged, the pivotal position being indicated by the position encoder regardless of the condition of the clutch.

When the hangers are not in use, couplings 90 and 92 are uncoupled and hangers 46 and 48 are usually fully retracted. The apparatus can be moved into position and coupled for conducting a lateral x-ray study as follows. A central microprocessor control first reads the position signal transmitted by the encoder associated with the length of hanger 44, and operates servomotor 303 for the bridge coupling mechanism to rotate coupling member 228 to the correct position for coupling with coupling member 230. Second, the image intensifier is manually extended or retracted to about the correct height and pivoted (with its clutch released) to approximately the correct position for the desired study. Servomotor 303 automatically compensates for any vertical travel of hanger 44 as already explained. Third, the image intensifier 24 is docked to bridge 88 and coupling members 228 and 230 are joined. Fourth, the microprocessor reads the position signals transmitted by the encoders associated with vertical travel of hanger 44 and pivotal travel of image intensifier, and operates the image intensifier pivoting stepping motor as necessary to precisely aim the longitudinal axis of image intensifier 24 through isocenter.

Next, the x-ray source 22 and associated hanger 42 and carriage 50 are manually operated to bring source 22 to approximately the proper height, coupling members 164 and 166 are juxtaposed, the height of source 22 is adjusted as necessary to line up the coupling members, and they are coupled. The microprocessor control is instructed to read the position signals transmitted by position encoders 192 and 420 to determine the height and pivotal position of x-ray source 22, and (with clutch 398 engaged) servomotor 356 is actuated as necessary to correlate the pivotal position of source 22 with its height, thereby aiming its central ray through isocenter.

Although a preferred mode of operation is described, it will be appreciated that other modes of operation could be practiced with the same apparatus within the scope of the present invention.

I claim:

1. A diagnostic x-ray machine for being mounted to a support to conduct fluoroscopic examinations with x-rays passing through an isocenter, said machine comprising:

an x-ray source for emitting a pattern of x-rays disposed about a central ray;

an x-ray source carriage for supporting said x-ray source, wherein said source carriage is supported by said support and mounted for pivoting said x-ray source about a first axis and for translating said x-ray source in a first plane perpendicular to said first axis;

an x-ray detector for receiving a pattern of x-rays from said source;

an x-ray detector carriage for supporting said x-ray detector, wherein said detector carriage is supported by said support and mounted for pivoting said x-ray detector about a second axis parallel to said first axis and for translating said x-ray detector in a second plane perpendicular to said second axis; and a bridge pivotally secured to said support for rotation about a third axis which is parallel to said first and second axes and passes through said isocenter, said bridge including coupling means for linking said x-ray source carriage and said x-ray detector carriage in such a way as to allow said x-ray source and x-ray detector to be maintained in diametric opposition with respect to said isocenter.

2. The machine of claim 1, wherein said coupling means can be disengaged to separate said x-ray source carriage and said x-ray detector carriage.

3. The machine of claim 1, wherein said means for supporting said x-ray source carriage by said support comprises first track means fixed to said support, second track means supported by and disposed orthogonally to said first track means and slidable along said first track means, and means for slidably supporting said x-ray source carriage on said second track means.

4. The machine of claim 1, wherein said means for supporting said x-ray detector carriage by said support comprises first track means fixed to said support, second track means supported by and disposed orthogonally to said first track means and slidable along said first track means, and means for slidably supporting said x-ray detector carriage on said second track means.

5. The machine according to claim 1, wherein said x-ray source carriage and x-ray detector carriage telescope along said first and second axes.

6. The machine according to claim 5, further comprising a first mechanical linkage coupling said telescoping carriages to translate proportional distances in opposite directions along said first and second axes.

7. The machine according to claim 6, further comprising means for pivoting said x-ray source and x-ray detector through equal and opposite angles proportional to translation of said source and detector along said first and second axes.

8. The machine according to claim 7, further comprising means to translate at least one of said x-ray source and detector toward and away from said isocenter without disturbing the diametric opposition of said source and said detector with respect to said isocenter.

9. The machine according to claim 8, further comprising a second mechanical linkage associated with said carriages for keeping the distance between said x-ray source and said isocenter and the distance between said x-ray detector and said isocenter constant for each selected source to image distance and each selected translational position of said source and said detector along said first and second axes.

10. The method according to claim 1, wherein said coupling means includes first coupling means and second coupling means, and said first coupling means comprises:
a first shaft having a first end supported by said bridge and a second end extending outwardly therefrom;
a first coupling member slidably captured on said first shaft;
a tubular member supported by said x-ray source carriage and having a first bore sized to slidably receive said first shaft in driving relation; and
a second coupling member secured to said tubular member and having means for releasably interlocking with said first coupling member;
interlocking of said first and second coupling members limiting the possible motion of said x-ray source carriage with respect to said bridge to translation along said first shaft.

11. The machine according to claim 10, wherein said second coupling means comprises:
a second shaft disposed parallel to said first shaft and having a first end supported by said bridge and a second end extending outwardly therefrom, said first and second shafts extending in opposite directions from said bridge;
a third coupling member slidably captured on said second shaft;
a second tubular member supported by said x-ray detector carriage and having a second bore sized to slidably receive said second shaft in driving relation, and
a fourth coupling member secured to said second tubular member and having means for releasably interlocking with said third coupling member;
interlocking of said third and fourth coupling members limiting the possible motion of said x-ray detector carriage with respect to said bridge to translation along said second shaft.

12. The machine according to claim 11, further comprising a first mechanical linkage wherein said first and second shafts are rotatably carried by said bridge, said first and third coupling members are splined to their respective shafts, said first and second tubular members are rotatably carried by the respective x-ray source and detector carriages, said x-ray source and detector carriages telescope to translate said x-ray source and detector along said first and second axes, said first and second shafts are linked so rotation of one said shaft results in coordinated rotation of the other said shaft, and said machine further comprises:
a first cable drum linked for rotation in coordination with rotation of said first shaft;
a first cable having a first end fixed with respect to said x-ray source and a second end reeved about said first cable drum;
a second cable drum linked for rotation in coordination with rotation of said second shaft; and
a second cable having a first end fixed with respect to said x-ray detector and a second end reeved about said second cable drum;
rotation of said first shaft in coordination with said first cable drum causing said first cable to wind on or unwind from said first drum to translate said x-ray source along said first axis, and rotation of said second drum in coordination with said second shaft winding or unwinding, respectively, said second cable on said second drum to translate said x-ray detector along said second axis a distance proportional to and in the opposite direction of the translation of said x-ray source along said first axis.

13. The machine according to claim 9, wherein said coupling means includes first and second coupling means, said machine including a second mechanical linkage comprising:
a guide fixed to said bridge and disposed perpendicularly to said first and second shafts;
a slide slidable on said guide;
a first link having a first end pivotally attached to said slide and a second end pivotally attached to said first coupling means,
a second link having a first end pivotally attached to said slide and a second end pivotally attached to said second coupling means; and
means for driving said slide along said guide
to move said x-ray source and detector carriages apart or together along said first and second shafts.

14. The machine according to claim 13, wherein said means to drive said slide comprises driven chain means and means for engaging said chain means with said first and second shafts.

15. The machine according to claim 10, including a second mechanical linkage comprising:
  a guide fixed to said bridge and disposed perpendicularly to said first and second shafts;
  a slide slidable on said guide;
  a first link having a first end pivotally attached to said slide and a second end pivotally attached to said first coupling means;
  a second link having a first end pivotally attached to said slide and a second end pivotally attached to said second coupling means; and
  means for driving said slide along said guide
  to move said x-ray source and detector carriages apart to together along said first and second shafts.

16. The machine according to claim 15, wherein said means to drive said slide comprises chain drive means and means for engaging said chain means with said first and second shafts.

17. A diagnostic x-ray machine for conducting lateral fluoroscopic examinations relative to a longitudinally extending patient supporting table top, comprising:
  two carriages each of which is mounted above said table top for moving longitudinally and laterally of the table top,
  a vertically extensible and contractible support device mounted to each carriage,
  an x-ray source mounted to one support device to angulate about a longitudinal axis and for emitting an x-ray beam having a central ray;
  an x-ray detector mounted to the other support to angulate about a longitudinal axis and for receiving an x-ray image produced by the beam from said source;
  bridge means mounted between said carriages for rotating about a vertical axis that intersects said central ray at a point defined as an isocenter, said bridge means having coupling means for releasably joining said carriages to selectively allow coordinated movement and independent movement of said carriages for the source and detector, respectively, and
  mechanisms on said bridge and carriages cooperating when said carriages and bridge are coupled to extend one of said support devices and contract the other device by equal amounts to alternatively raise and lower said source and detector by equal amounts and simultaneously turn said x-ray source and detector through equal and opposite angles proportional to the amount said source and detector are raised and lowered to maintain intersection of said central ray with said rotational axis of the bridge at said isocenter.

18. The machine according to claim 17, wherein said coupling means comprises first and second couplings, said first coupling releasably joining the mechanism in the bridge with the mechanism in the carriage that carries said x-ray source, said second coupling releasably joining the mechanism in the bridge with the mechanism in the carriage that carries said x-ray detector.

19. The machine according to claim 17, wherein said carriage for said x-ray source and carriage for said detector are independently supported, the means for supporting a carriage comprising fixedly mounted track means arranged in a horizontal plane, a first truck mounted to said track means for moving in one line, a second truck mounted to said first truck for moving along a line perpendicular to said one line such that when said carriages are coupled to said bridge and said bridge is rotated about said vertical axis said trucks will move jointly and each carriage will travel along an arc disposed about said vertical axis.

20. The machine according to claim 17, wherein said mechanism includes first linking means for coordinating the extension and retraction of said source and detector or support devices.

21. The machine according to claim 20, wherein said bridge means includes third and fourth telescoping members extending in opposite directions along a another axis which is normal to said vertical axis, said mechanism including means to extend and retract said telescoping for translating said x-ray source and said detector members parallel to said other axis.

22. The machine according to claim 21, wherein said mechanism includes second linking means for coordinating the extension and retraction of said telescoping members.

23. The machine according to claim 22, wherein said first and second linking means are operatively connected for controlling the components of movement of said source and detector parallel to said vertical axis and parallel to said normal axes so said source and detector are each constrained to follow the surface of a sphere having its center at said isocenter.

* * * * *